United States Patent
Kinouchi et al.

(10) Patent No.: US 7,429,244 B2
(45) Date of Patent: Sep. 30, 2008

(54) BLOOD-VESSEL-SHAPE MEASURING APPARATUS, BLOOD-FLOW-VELOCITY MEASURING APPARATUS, AND BLOOD-FLOW-AMOUNT MEASURING APPARATUS

(75) Inventors: Yohsuke Kinouchi, Tokushima (JP); Hitoshi Hirano, Nagoya (JP)

(73) Assignees: Unex Corporation, Nagoya (JP); The University of Tokushima, Tokushima (JP)

( * ) Notice: Subject to any disclaimer, the term of this patent is extended or adjusted under 35 U.S.C. 154(b) by 168 days.

(21) Appl. No.: 10/565,675

(22) PCT Filed: Jul. 28, 2005

(86) PCT No.: PCT/JP2005/013813
§ 371 (c)(1),
(2), (4) Date: Feb. 3, 2006

(87) PCT Pub. No.: WO2006/011544
PCT Pub. Date: Feb. 2, 2006

(65) Prior Publication Data
US 2006/0241427 A1 Oct. 26, 2006

(30) Foreign Application Priority Data
Jul. 28, 2004 (JP) .................... 2004-219866

(51) Int. Cl.
*A61B 8/00* (2006.01)
(52) U.S. Cl. ............... 600/437; 600/459
(58) Field of Classification Search ............ 600/459, 600/437, 409
See application file for complete search history.

(56) References Cited

U.S. PATENT DOCUMENTS

| 5,339,816 A | * | 8/1994 | Akamatsu et al. | ........... 600/455 |
| 5,515,857 A | | 5/1996 | Tsujino et al. | |
| 5,891,039 A | * | 4/1999 | Bonnefous et al. | .......... 600/454 |
| 6,261,233 B1 | * | 7/2001 | Kantorovich | ............... 600/454 |

(Continued)

FOREIGN PATENT DOCUMENTS

JP    A-05-056971    3/1993

(Continued)

*Primary Examiner*—Eric F Winakur
*Assistant Examiner*—Katherine L Fernandez
(74) *Attorney, Agent, or Firm*—Oliff & Berridge, PLC

(57) ABSTRACT

A blood-vessel-shape measuring apparatus that can accurately measures a shape of a section of a blood vessel is provided.

A blood-vessel-shape calculating means 62 calculates, based on respective echo signals detected by first and second arrays 26, 28 that are placed on a skin 20 of a brachial portion 14 as a portion of a living being such that each of the first and second arrays 26, 28 is across a brachial artery 18 located under the skin 20, respective positions of respective portions of the arterial wall that are located right below the first and second arrays 26, 28 and correspond to supersonic-wave elements $26_n$ of the first array 26 and supersonic-wave elements $28_n$ of the second array 28, and calculates, based on the respective positions of the respective portions of the arterial wall that correspond to the supersonic-wave elements $26_n$, $28_n$, a shape of the brachial artery 18 on an orthogonal section thereof. Thus, even if the brachial artery 18 may run, under the skin 20, in a direction that is not orthogonal to the first or second array 26, 28 or is not parallel to the skin 20, an accurate sectional shape of the brachial artery 18 can be obtained.

12 Claims, 8 Drawing Sheets

U.S. PATENT DOCUMENTS 6,663,568 B1  12/2003  Gill
2003/0114756 A1 *  6/2003  Li ............................. 600/437

FOREIGN PATENT DOCUMENTS

| JP | A-07-023951 | 1/1995 |
| JP | A-10-192278 | 7/1998 |
| JP | A-11-076233 | 3/1999 |
| JP | A-2002-011008 | 1/2002 |
| JP | A-2002-505901 | 2/2002 |

* cited by examiner

BLOOD-VESSEL-SHAPE MEASURING APPARATUS, BLOOD-FLOW-VELOCITY MEASURING APPARATUS, AND BLOOD-FLOW-AMOUNT MEASURING APPARATUS

TECHNICAL FIELD

The present invention relates to an apparatus for measuring, with a supersonic wave, a shape of a blood vessel located under a skin of a living being, a blood-flow-velocity measuring apparatus for measuring a velocity of a blood flow in a blood vessel, and a blood-flow-amount measuring apparatus for measuring an amount of a blood flow in a blood vessel.

BACKGROUND ART

There is a need to measure non-invasively and accurately a diameter or a sectional area of a blood vessel of a living being, a velocity of a blood flow in a blood vessel, or an amount of a blood flow in a blood vessel, for the purpose of examining the condition of the living being. For example, when the condition of endothelium of an artery having an inner diameter of 4 mm is examined, it is needed to measure, with allowable errors of 1%, a diameter or a sectional area of the artery, a velocity of a blood flow in the artery, or an amount of a blood flow in the artery.

Patent Document 1 proposes non-invasively placing a first array including a plurality of first supersonic-wave elements arranged in one direction, and a second array including a plurality of second supersonic-wave elements arranged in a direction parallel to said one direction, such that the first and second arrays are respectively located at two positions distant from each other in a lengthwise direction of a blood vessel located under a skin of a living being, and detecting respective shapes of respective sections of the blood vessel that correspond to the two positions, respectively. According to this technique, a supersonic wave is utilized and accordingly a sectional shape of a blood vessel can be detected non-invasively.

Patent Document 1: Japanese Patent Application Publication No. 11-76233

DISCLOSURE OF THE INVENTION

PROBLEM SOLVED BY THE INVENTION

However, since the above-indicated conventional, blood-vessel sectional-shape detecting device detects the respective sectional shapes of the blood vessel on a measuring section containing the direction of arrangement of the first supersonic-wave elements of the first array and a measuring section containing the direction of arrangement of the second supersonic-wave elements of the second array, those measuring sections do not always intersect orthogonally the lengthwise direction of the blood vessel and accordingly the detected sectional shapes of the blood vessel may not be sufficiently accurate. When a supersonic-wave probe to which the first and second arrays are fixed is worn on a skin of a living being under which an artery runs, an operator cannot easily see a position of the artery and accordingly cannot accurately wear the first and second arrays on the skin such that the first and second arrays extend perpendicularly to the artery. In addition, since in many cases an artery does not run parallel to a skin, a lengthwise direction of the artery does not orthogonally intersect the respective measuring sections of the first and second arrays. Thus, respective sectional shapes of the blood vessel, such as respective diameters or respective sectional areas of the blood vessel on the respective measuring sections, or a velocity or an amount of a blood flow calculated based on the sectional shape cannot be accurately measured.

It is therefore an object of the present invention to provide a blood-vessel-shape measuring apparatus, a blood-flow-velocity measuring apparatus, and a blood-flow-amount measuring apparatus that can accurately measure a shape of a blood vessel, a velocity of a blood vessel in a blood vessel, and an amount of a blood vessel in a blood vessel, respectively.

SOLUTION TO PROBLEM

The above-indicated object is achieved by an invention, recited in claim 1, that is related to a blood-vessel-shape measuring apparatus comprising a first array including a plurality of first supersonic-wave elements arranged in one direction; and a second array including a plurality of second supersonic-wave elements arranged in a direction parallel to said one direction, the apparatus measuring a shape of a blood vessel of a living being, based on echo signals detected by the first and second arrays that are placed on a skin of the living being such that each of the first and second arrays is across the blood vessel located under the skin, the apparatus further comprising (a) a first wall-position calculating means for calculating, based on respective reflection signals detected by the first supersonic-wave elements of the first array, respective positions of respective portions of a wall of the blood vessel that are located right below the first array and correspond to the first supersonic-wave elements; (b) a second wall-position calculating means for calculating, based on respective echo signals detected by the second supersonic-wave elements of the second array, respective positions of respective portions of the wall of the blood vessel that are located right below the second array and correspond to the second supersonic-wave elements; and (c) a blood-vessel-shape calculating means for calculating a shape of the blood vessel on an orthogonal section thereof, based on the respective positions of the respective portions of the wall of the blood vessel that correspond to the first supersonic-wave elements and are calculated by the first wall-position calculating means, and the respective positions of the respective portions of the wall of the blood vessel that correspond to the first supersonic-wave elements and are calculated by the second wall-position calculating means.

In an invention, recited in claim 2 depending from claim 1, (a) the first wall-position calculating means calculates respective distances to the respective portions of the wall of the blood vessel, based on respective time differences between respective emission signals emitted by the first supersonic-wave elements and the respective reflection signals from the respective portions of the wall, detected by the first supersonic-wave elements, and determines, based on the calculated respective distances, the respective positions of the respective portions of the wall on a measuring section of the first array, and (b) the second wall-position calculating means calculates respective distances to the respective portions of the wall of the blood vessel, based on respective time differences between respective emission signals emitted by the second supersonic-wave elements and respective reflection signals from the respective portions of the wall, detected by the second supersonic-wave elements, and determines, based on the calculated respective distances, the respective positions of the respective portions of the wall on a measuring section of the second array.

In an invention, recited in claim 3 depending from claim 2, the blood-vessel-shape calculating means comprises (a) a measuring-section-shape calculating means for calculating, based on the respective positions of the respective portions of the wall of the blood vessel that correspond to the first supersonic-wave elements and are calculated by the first wall-position calculating means, and the respective positions of the respective portions of the wall of the blood vessel that correspond to the second supersonic-wave elements and are calculated by the second wall-position calculating means, a center point, and a major-axis length and/or a minor-axis length, of each of a section of the wall of the blood vessel on the measuring section of the first array and a section of the wall of the blood vessel on the measuring section of the second array; (b) a center-axis calculating means for calculating a center axis of the blood vessel, based on the respective center points of the respective sections of the wall of the blood vessel on the respective measuring sections of the first and second arrays, calculated by the measuring-section shape calculating means; (c) a cross-angle calculating means for calculating, based on the center axis of the blood vessel, calculated by the center-axis calculating means, a cross angle at which the orthogonal section of the blood vessel and the measuring section cross each other; and (d) a correcting means for correcting, based on the cross angle calculated by the cross-angle calculating means, the major-axis length and/or the minor-axis length calculated by the measuring-section-shape calculating means, into a corrected major-axis length and/or a corrected minor-axis length on the orthogonal section of the blood vessel.

In an invention, recited in claim 4 depending from claim 3, the blood-vessel-shape calculating means comprises an orthogonal-section-area calculating means for calculating an area of the section of the blood vessel on the orthogonal section thereof, based on the corrected major-axis length and the corrected minor-axis length provided by the correcting means.

The above-indicated object is achieved by an invention, recited in claim 5, that is related to a blood-flow-velocity measuring apparatus, comprising (a) a supersonic-wave probe including a first array including a plurality of first supersonic-wave elements arranged in one direction, a second array including a plurality of second supersonic-wave elements arranged in a direction parallel to said one direction, and a Doppler supersonic-wave element, the supersonic-wave probe being worn such that each of the first and second arrays is across a blood vessel located under a skin of a living being and a direction in which the Doppler supersonic-wave element emits a supersonic wave has an acute angle with respect to the blood vessel; (b) a blood-flow-velocity calculating means for calculating, based on a Doppler reflection wave which is obtained when the Doppler supersonic-wave element emits the supersonic wave toward the blood vessel and which is changed by a Doppler effect based on a velocity of a blood flow in the blood vessel, the velocity of the blood flow; (c) a first wall-position calculating means for calculating, based on respective reflection signals detected by the first supersonic-wave elements of the first array, respective positions of respective portions of a wall of the blood vessel that are located right below the first array and correspond to the first supersonic-wave elements; (d) a second wall-position calculating means for calculating, based on respective echo signals detected by the second supersonic-wave elements of the second array, respective positions of respective portions of the wall of the blood vessel that are located right below the second array and correspond to the second supersonic-wave elements; (e) a center-axis calculating means for calculating, based on the respective positions of the respective portions of the wall of the blood vessel that correspond to the first supersonic-wave elements and are calculated by the first wall-position calculating means, and the respective positions of the respective portions of the wall of the blood vessel that correspond to the second supersonic-wave elements and are calculated by the second wall-position calculating means, respective center points of respective sections of the wall of the blood vessel on the respective measuring sections of the first and second arrays, and calculating a center axis of the blood vessel, based on the respective center points of the respective sections of the wall of the blood vessel on the respective measuring sections of the first and second arrays; (f) a relative-angle calculating means for calculating an actual relative angle between the center axis of the blood vessel, calculated by the center axis calculating means, and the direction in which the Doppler supersonic-wave element emits the supersonic wave toward the blood vessel; and (g) a blood-flow-velocity correcting means for correcting, based on the actual relative angle calculated by the relative-angle calculating means, the velocity of the blood flow calculated by the blood-flow-velocity calculating means.

The above-indicated object is achieved by an invention, recited in claim 6, that is related to a blood-flow-amount measuring apparatus, characterized by comprising (a) the blood-flow-velocity measuring apparatus according to claim 5; (b) a measuring-section-shape calculating means for calculating, based on the respective positions of the respective portions of the wall of the blood vessel that correspond to the first supersonic-wave elements and are calculated by the first wall-position calculating means, and the respective positions of the respective portions of the wall of the blood vessel that correspond to the second supersonic-wave elements and are calculated by the second wall-position calculating means, a center point, and a major-axis length and/or a minor-axis length, of each of a section of the wall of the blood vessel on the measuring section of the first array and a section of the wall of the blood vessel on the measuring section of the second array; (c) a cross-angle calculating means for calculating, based on the center axis of the blood vessel, calculated by the center-axis calculating means, a cross angle at which the orthogonal section of the blood vessel and the measuring section cross each other; (d) a correcting means for correcting, based on the cross angle calculated by the cross-angle calculating means, the major-axis length and/or the minor-axis length calculated by the measuring-section-shape calculating means, into a corrected major-axis length and/or a corrected minor-axis length on the orthogonal section of the blood vessel; (e) an orthogonal-section-area calculating means for calculating an area of the section of the blood vessel on the orthogonal section thereof, based on the corrected major-axis length and the corrected minor-axis length provided by the correcting means; and (f) a blood-flow-amount calculating means for calculating an amount of the blood flow in the blood vessel, based on the area of the section of the blood vessel on the orthogonal section thereof calculated by the orthogonal-section-area calculating means, and the velocity of the blood flow corrected by the blood-flow-velocity correcting means.

ADVANTAGE OF THE INVENTION

According to the invention recited in claim 1, the blood-vessel-shape calculating means calculates, based on the echo signals detected by the first and second arrays that are placed on the skin of the living being such that each of the first and second arrays is across the blood vessel located under the skin, the respective positions of the respective portions of the wall of the blood vessel that are located right below the first and second arrays and correspond to the first and second supersonic-wave elements, and additionally calculates, based on the respective positions of the respective portions of the wall that correspond to the first and second supersonic-wave elements, the shape of the blood vessel on the orthogonal section thereof. Thus, even if the blood vessel of the living being may run, under the skin, in a direction that is not orthogonal to the first or second array or is not parallel to the skin, an accurate sectional shape of the blood vessel, such as a diameter, a sectional contour, or a sectional area, can be obtained.

According to the invention recited in claim 2, the first wall-position calculating means calculates the respective distances to the respective portions of the wall of the blood vessel, based on the respective time differences between the respective emission signals emitted by the first supersonic-wave elements and the respective reflection signals from the respective portions of the wall, detected by the first supersonic-wave elements, and the second wall-position calculating means calculates the respective distances to the respective portions of the wall, based on the respective time differences between the respective emission signals emitted by the second supersonic-wave elements and the respective reflection signals from the respective portions of the wall, detected by the second supersonic-wave elements. The blood-vessel-shape calculating means determines, based on the thus calculated respective distances, the respective positions of the respective portions of the wall on the measuring section of the first array. Thus, the respective positions of the respective portions of the wall of the blood vessel on each of the respective measuring sections of the first and second arrays can be obtained with accuracy.

According to the invention recited in claim 3, the blood-vessel-shape calculating means calculates, based on the respective positions of the respective portions of the wall of the blood vessel on each of the respective measuring sections of the first and second arrays, the center point, and the major-axis length and/or the minor-axis length, of each of the respective sections of the wall on the respective measuring sections of the first and second arrays, then calculates the center axis of the blood vessel, based on the respective center points of the respective sections of the wall on the respective measuring sections of the first and second arrays, subsequently calculates, based on the center axis of the blood vessel, the cross angle at which the orthogonal section of the blood vessel and the measuring section cross each other, and finally corrects, based on the cross angle, the major-axis length and/or the minor-axis length, into the corrected major-axis length and/or the corrected minor-axis length on the orthogonal section of the blood vessel. Thus, even if the blood vessel may run, under the skin, in a direction that is not orthogonal to the first or second array or is not parallel to the skin, an accurate sectional shape of the blood vessel can be obtained.

According to the invention recited in claim 4, the blood-vessel-shape calculating means comprises the orthogonal-section-area calculating means that calculates the sectional area of the blood vessel on the orthogonal section thereof, based on the corrected major-axis length and the corrected minor-axis length provided by the correcting means. Thus, even if the blood vessel of the living being may run, under the skin, in a direction that is not orthogonal to the first or second array or is not parallel to the skin, an accurate sectional area of the blood vessel can be obtained.

According to the invention recited in claim 5, the blood-flow-velocity measuring apparatus comprises (a) the supersonic-wave probe including the first array including the plurality of first supersonic-wave elements arranged in one direction, the second array including the plurality of second supersonic-wave elements arranged in the direction parallel to the one direction, and the Doppler supersonic-wave element, the supersonic-wave probe being worn such that each of the first and second arrays is across the blood vessel located under the skin of the living being and the direction in which the Doppler supersonic-wave element emits the supersonic wave has the acute angle with respect to the blood vessel; (b) the blood-flow-velocity calculating means that calculates, based on the Doppler reflection wave that is obtained when the Doppler supersonic-wave element emits the supersonic wave toward the blood vessel and that is changed by a Doppler effect based on a velocity of a blood flow in the blood vessel, the velocity of the blood flow; (c) the first wall-position calculating means that calculates, based on the respective reflection signals detected by the first supersonic-wave elements of the first array, the respective positions of the respective portions of the wall of the blood vessel that are located right below the first array and correspond to the first supersonic-wave elements; (d) the second wall-position calculating means that calculates, based on the respective echo signals detected by the second supersonic-wave elements of the second array, the respective positions of the respective portions of the wall that are located right below the second array and correspond to the second supersonic-wave elements; (e) the center-axis calculating means that calculates, based on the respective positions of the respective portions of the wall, calculated by the first wall-position calculating means, and the respective positions of the respective portions of the wall, calculated by the second wall-position calculating means, the respective center points of the respective sections of the wall on the respective measuring sections of the first and second arrays, and calculates the center axis of the blood vessel based on the respective center points of the respective sections of the wall on the respective measuring sections of the first and second arrays; (f) the relative-angle calculating means that calculates the actual relative angle between the center axis of the blood vessel, calculated by the center-axis calculating means, and the direction in which the Doppler supersonic-wave element emits the supersonic wave toward the blood vessel; and (g) the blood-flow-velocity correcting means that corrects, based on the actual relative angle calculated by the relative-angle calculating means, the velocity of the blood flow calculated by the blood-flow-velocity calculating means. Thus, even if the blood vessel of the living being may run, under the skin, in a direction that is not orthogonal to the first or second array or is not parallel to the skin, an accurate blood flow velocity in the blood vessel can be obtained.

According to the invention recited in claim 6, the blood-flow-amount measuring apparatus comprises (a) the blood-flow-velocity measuring apparatus according to claim 5; (b) the measuring-section-shape calculating means that calculates, based on the respective positions of the respective portions of the wall of the blood vessel, calculated by the first wall-position calculating means, and the respective positions of the respective portions of the wall, calculated by the second wall-position calculating means, the center point and the major-axis length and the minor-axis length, of each of the respective sections of the wall on the respective measuring sections of the first and second arrays; (c) the cross-angle calculating means that calculates, based on the center axis of the blood vessel, calculated by the center-axis calculating means, the cross angle at which the orthogonal section of the blood vessel and the measuring section cross each other; (d) the correcting means that corrects, based on the cross angle calculated by the cross-angle calculating means, the major-axis length and the minor-axis length calculated by the measuring-section-shape calculating means, into a corrected major-axis length and a corrected minor-axis length on the orthogonal section of the blood vessel; (e) the orthogonal-section-area calculating means that calculates the sectional area of the blood vessel on the orthogonal section thereof, based on the corrected major-axis length and the corrected minor-axis length provided by the correcting means; and (f) the blood-flow-amount calculating means that calculates the amount of the blood flow in the blood vessel based on the sectional area of the blood vessel on the orthogonal section thereof, calculated by the orthogonal-section-area calculating means, and the blood flow velocity corrected by the blood-flow-velocity correcting means. Thus, even if the blood vessel of the living being may run, under the skin, in a direction that is not orthogonal to the first or second array or is not parallel to the skin, an accurate blood flow amount in the blood vessel can be obtained.

BEST MODE FOR CARRYING OUT THE INVENTION

Preferably, the blood vessel is an artery located under the skin of the living being, such as a brachial artery, a radial artery, a dorsal pedal artery, a carotid artery, or a superficial temporal artery. When FMD (flow-mediated dilation, i.e., endothelium-dependent dilation) is carried out, the present invention is applied to, e.g., a brachial artery, a radial artery, or a dorsal pedal artery; and when a blood flow to the cerebrovascular system is examined, the present invention is applied to, e.g., a carotid artery, or a superficial temporal artery.

Preferably, each of the supersonic-wave elements of the first and second arrays may be one employing a common oscillator that functions as not only a transmitter but also a receiver, or one employing both a transmitter and a receiver.

Preferably, the Doppler supersonic-wave element may be one employing a common oscillator that functions as not only a transmitter but also a receiver, or one employing both a transmitter and a receiver. In addition, the Doppler supersonic-wave element may be constituted by an array of oscillators that are arranged in a direction across the direction in which the blood vessel runs.

EMBODIMENT

Figure 1:
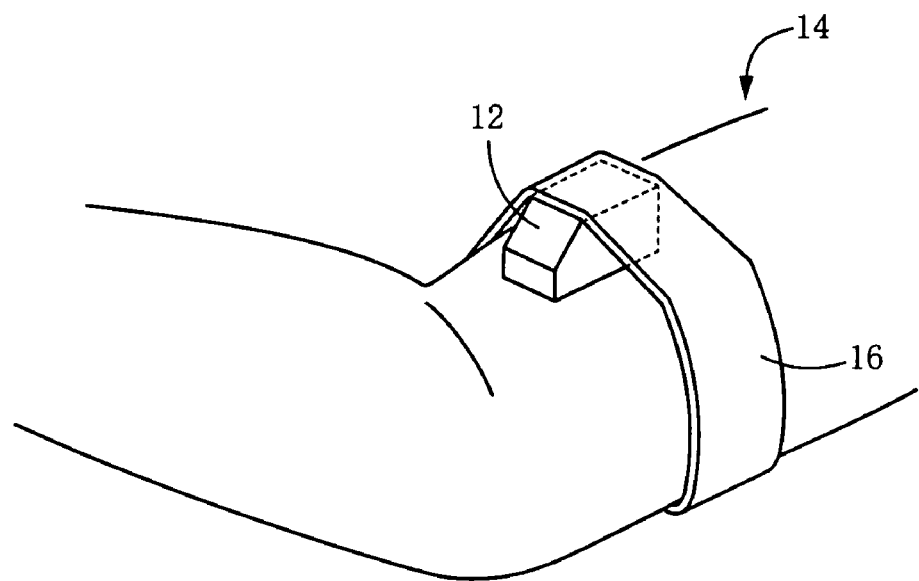
FIG. 1 is a perspective view showing a state in which a supersonic-wave probe employed by a supersonic-wave measuring apparatus as an embodiment of the present invention is worn on an upper arm.
Figure 2:
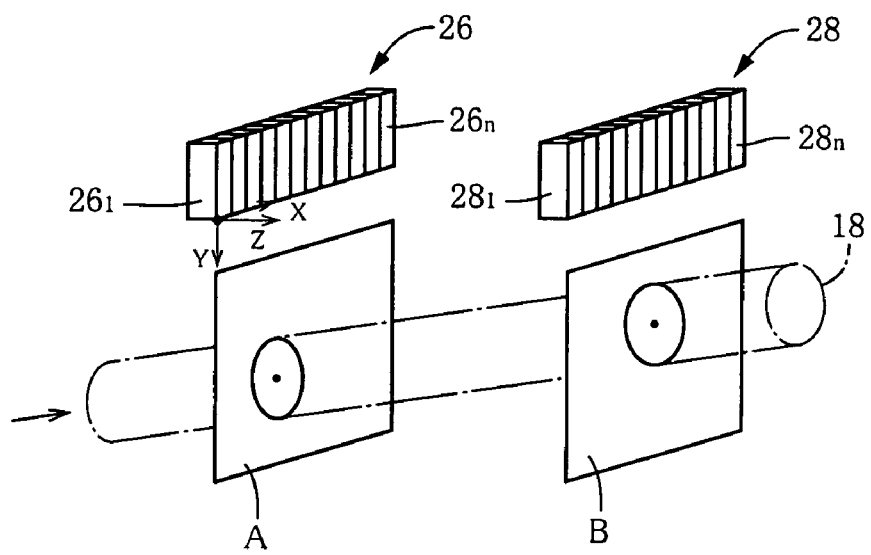
FIG. 2 is a perspective view showing a relationship between each of respective measuring sections of a first array and a second array employed by the supersonic-wave probe of the supersonic-wave measuring apparatus of FIG. 1, and a brachial artery.
Figure 3:
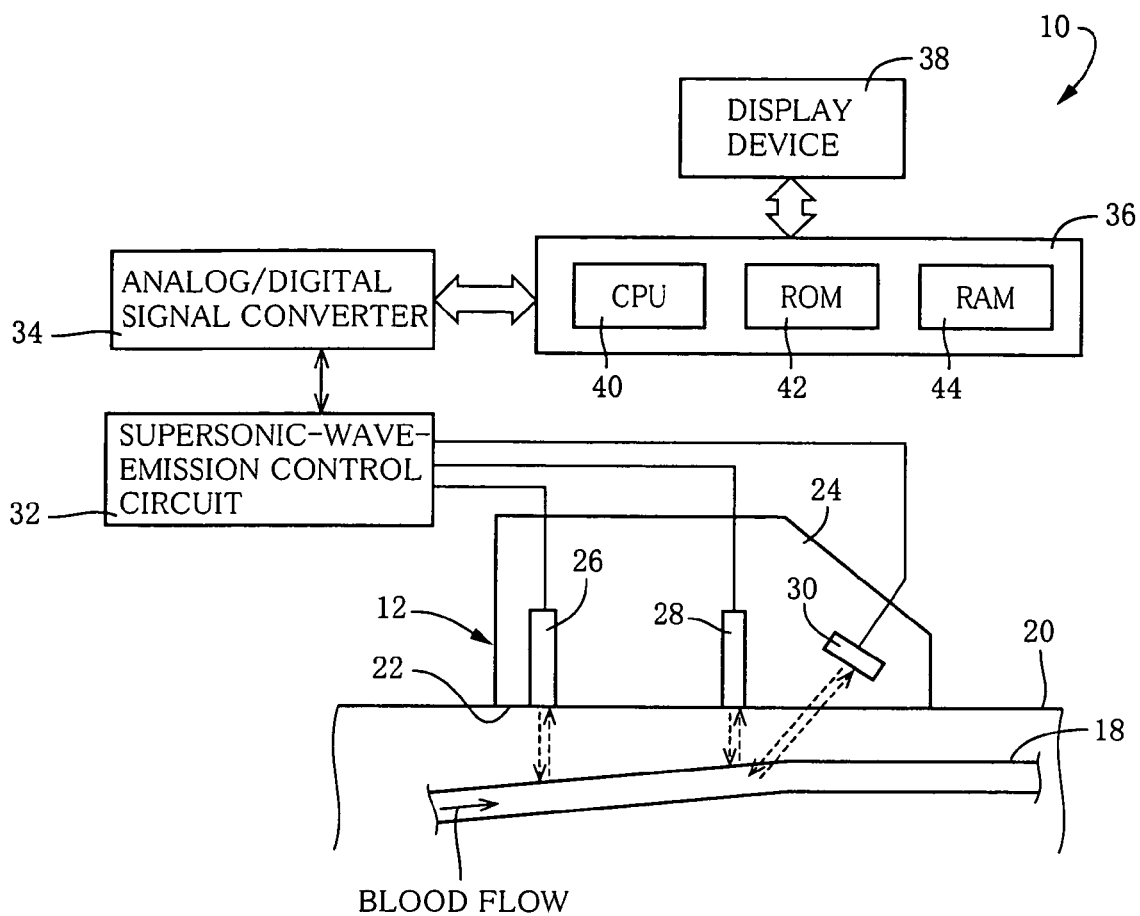
FIG. 3 is a view for explaining a construction of the supersonic-wave measuring apparatus of FIG. 1.

Hereinafter, there will be described a preferred embodiment of the present invention in detail by reference to the drawings. FIG. 1 shows a state in which a supersonic-wave probe 12 employed by a supersonic-wave measuring apparatus 10 as an embodiment of the present invention is worn on a living being. As shown in FIG. 2 or FIG. 3, the supersonic-wave probe 12 is worn, with a wearing band 16, on a portion of the living being, for example, at a position right above a brachial artery 18 of a brachial portion 14 of the living being. The brachial artery 18 has such a shape that the artery 18 extends from a lower side of a lower end of a biceps muscle of arm toward a skin 20.

The supersonic-wave probe 12 has a contact surface 22 that is adapted to contact the skin 20, and includes a main body 24 that is formed of a supersonic-wave transmitting material such as a synthetic resin (e.g., an acrylic resin), a ceramic material, or a metal; an elongate first array 26 and an elongate second array 28 that are embedded in the main body 24 such that the first and second arrays 28 are parallel to each other, distant from each other by a predetermined distance, L (FIG. 7 or FIG. 8), and each across the brachial artery 18; and an elongate third array 30 that is provided on a downstream side of the second array 28, across the brachial artery 18. The first array 26 includes a plurality of supersonic-wave elements $26_n$ (n is an integral number) that are arranged in a lengthwise direction thereof; and the second array 28 includes a plurality of supersonic-wave elements $28_n$ that are arranged in a lengthwise direction thereof. The third array 30 also includes a plurality of supersonic-wave elements $30_n$ that are arranged in a lengthwise direction thereof parallel to the first and second arrays 26, 28. The supersonic-wave elements $26_n$ are arranged at a regular interval of, e.g., from 0.2 mm to 0.5 mm that is sufficiently smaller than a diameter of the brachial artery 18 as a measuring object; and the supersonic-wave elements $28_n$ are arranged at the same regular interval. The supersonic-wave elements $30_n$ are arranged at the same regular interval, or a greater regular interval.

Each of the supersonic-wave elements $26_n$ of the first array 26 and the supersonic-wave elements $28_n$ of the second array 28 is constituted by a piezoelectric element, and functions as both an emitter and a receiver that emits and receives a supersonic wave. Each supersonic-wave element $26_n$, $28_n$ is oriented perpendicularly to the contact surface 22 so as to be able to emit a supersonic wave in a downward direction. Each of the supersonic-wave elements $30_n$ of the third array 30 is constituted by a piezoelectric element, and functions as both an emitter and a receiver that emits and receives a supersonic wave. A supersonic-wave emission surface of each supersonic-wave element $30_n$ is inclined by, e.g., 45 degrees, with respect to the contact surface 22 so as to be able to emit a supersonic wave toward an upstream portion of the brachial artery 18. The supersonic-wave elements $26_n$ of the first array 26 and the supersonic-wave elements $28_n$ of the second array 28 are provided such that the elements $26_n$, $28_n$ are located along the contact surface 22 defined as an X-Z plane; and a supersonic-wave element $26_1$ located at an end of the supersonic-wave elements $26_n$ of the first array 26 is defined as an origin of an X-Y-Z three-dimensional orthogonal plane.

Each of the supersonic-wave elements $26_n$ of the first array 26 and the supersonic-wave elements $28_n$ of the second array 28 emits a supersonic wave in a direction perpendicular to the contact surface 22, and receives, as an echo signal, the wave reflected from an interface present in a way of propagation of the supersonic wave. Therefore, as shown in FIG. 2, right below the first array 26 and the second array 28, there are formed a measuring section A and a measuring section B, respectively, which are parallel to each other and each of which intersects the brachial artery 18. Each of the measuring section A and the measuring section B is parallel to an X-Y plane of the X-Y-Z three-dimensional orthogonal plane, and an arbitrary position on the each measuring section A, B is expressed as coordinates.

As shown in FIG. 3, the supersonic-wave measuring apparatus 10 includes a supersonic-wave-emission control circuit 32 that controls the first array 26, the second array 28, and the third array 30; an analog/digital signal converter 34 that converts one of an analog signal and a digital signal into the other signal; an electronic control device 36; and a display device 38 that displays numerals and images. The electronic control device 36 is constituted by a so-called microcomputer including a CPU 40, a ROM 42, a RAM 44, a memory device, not shown, and an interface, not shown. The CPU 40 processes input signals according to a control program pre-stored by the ROM 42, while utilizing a temporary-storage function of the RAM 44, and calculates a shape of a blood vessel, a velocity of a blood flow, and an amount of a blood flow. In addition, the CPU 40 controls the display device 38 to display those calculation results. Therefore, the supersonic-wave measuring apparatus 10 functions as each of a blood-vessel-shape measuring apparatus, a blood-flow-velocity measuring apparatus, and a blood-flow-amount measuring apparatus.

Figure 4:
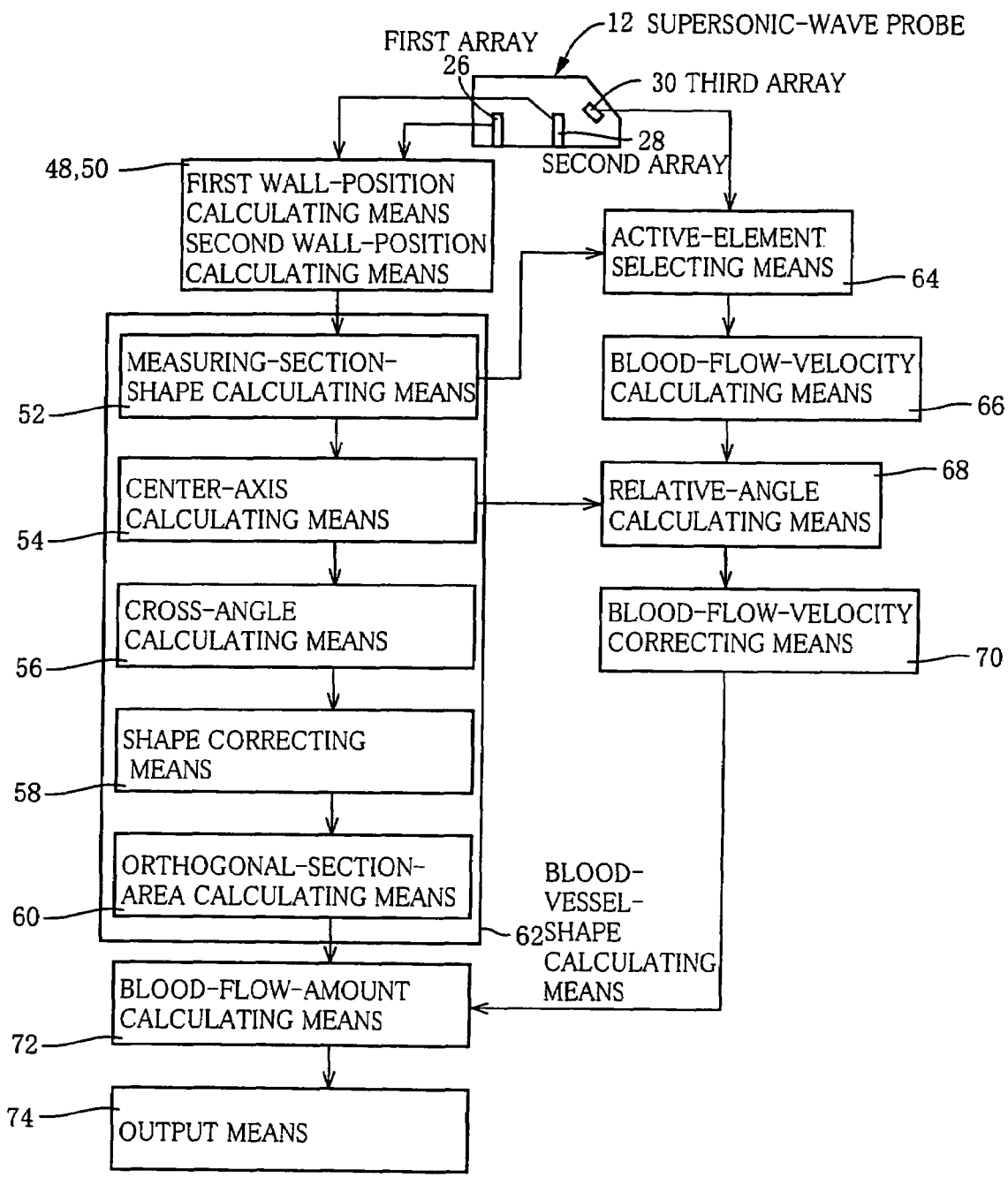
FIG. 4 is a block diagram for explaining various functional portions of an electronic control device, shown in FIG. 3.
Figure 5:
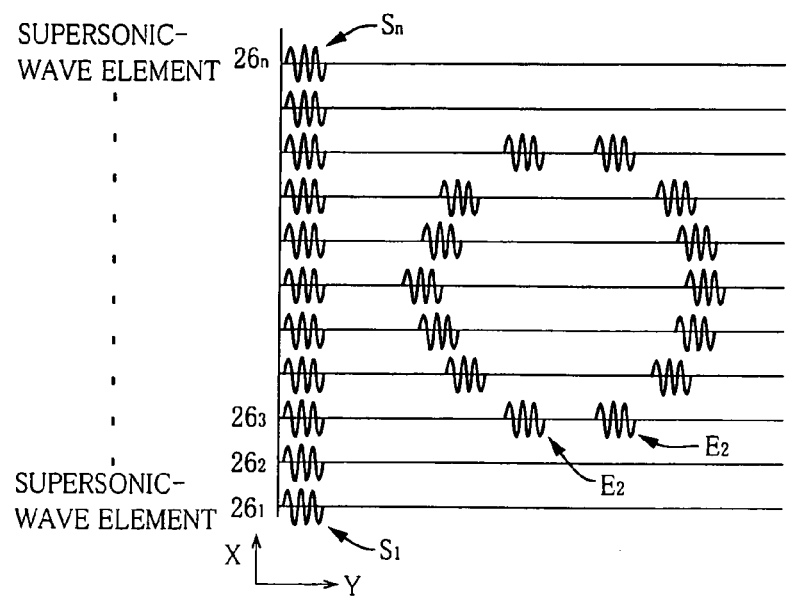
FIG. 5 is a view for explaining respective waves emitted and received by supersonic-wave elements, on the measuring section of the first array.

FIG. 4 is a block diagram for explaining various control functions of the electronic control device 36. In FIG. 4, a first wall-position calculating means or device 48 calculates, based on the respective echo signals received by the supersonic-wave elements $26_n$, a sectional shape of the brachial artery 18, taken along the measuring section A right below the first array 26; and a second wall-position calculating means or device 50 calculates, based on the respective echo signals received by the supersonic-wave elements $28_n$, a sectional shape of the brachial artery 18, taken along the measuring section B right below the second array 28. FIG. 5 shows a time chart showing respective waveforms of respective emission signals, $S_n$, emitted by the supersonic-wave elements $26_n$ of the first array 26, and respective waveforms of respective echo signals, $E_n$, reflected from the wall of the brachial artery 18. A time difference between each of the emission signals $S_n$ and a corresponding one of the echo signals $E_n$ corresponds to a depth of a corresponding one of portions of the arterial wall as measured from the first array 26. Thus, the first wall-position calculating means 48 iteratively calculates, based on the respective time differences between the respective emission signals $S_n$ and the corresponding echo signals $E_n$ and a velocity of a sound propagating in a vital tissue, respective depth positions of the respective portions of the arterial wall that correspond to the supersonic-wave elements $26_n$. Likewise, the second wall-position calculating means 50 iteratively calculates respective depth positions of respective portions of the arterial wall that correspond to the supersonic-wave elements $28_n$.

Figure 6:
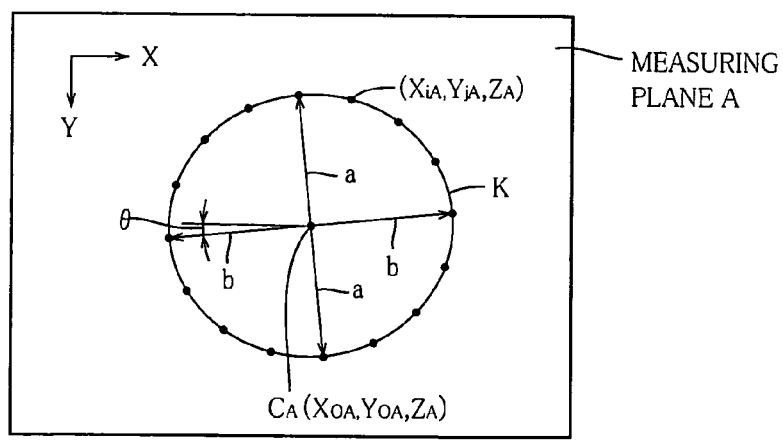
FIG. 6 is a view for explaining respective coordinates of respective points on the measuring section of the first array, calculated by a first wall-position calculating means, shown in FIG. 4, based on respective time differences between the emitted waves and the received waves, shown in FIG. 5, and a shape of a lumen of the brachial artery as a closed curved line obtained by connecting those points to each other.

A measuring-section-shape calculating means or device 52 expresses the respective depth positions of the respective portions of the arterial wall that correspond to the supersonic-wave elements $26_n$, in terms of respective points on an X-Y coordinate plane, as shown in FIG. 6, that corresponds to the measuring section A and, likewise, expresses the respective depth positions of the respective portions of the arterial wall that correspond to the supersonic-wave elements $28_n$, in terms of respective points on an X-Y coordinate plane corresponding to the measuring section B. In addition, the measuring-section-shape calculating means 52 iteratively calculates a closed curved line, K, by interpolating, on each of the measuring sections A, B, the thus obtained points with curved segments, and determines the thus obtained closed line K as a shape of a lumen of the brachial artery 18 on the each measuring section A, B. Moreover, the measuring-section-shape calculating means 52 iteratively calculates a length, $2b$, of a major axis of each of the two closed lines K, a length, $2a$, of a minor axis of the each closed line K, and an angle of inclination of the major axis with respect to the X axis.

Figure 7:
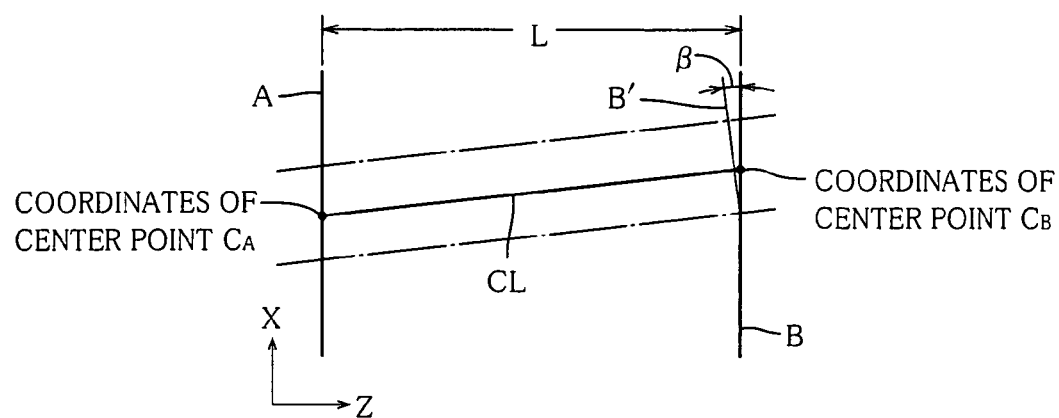
FIG. 7 is a view for explaining a cross angle, $\beta$, at which an orthogonal section B' orthogonal to a center axis CL obtained by a center-axis calculating means, shown in FIG. 4, and the measuring section B of the second array cross each other on a plane parallel to a contact surface.
Figure 8:
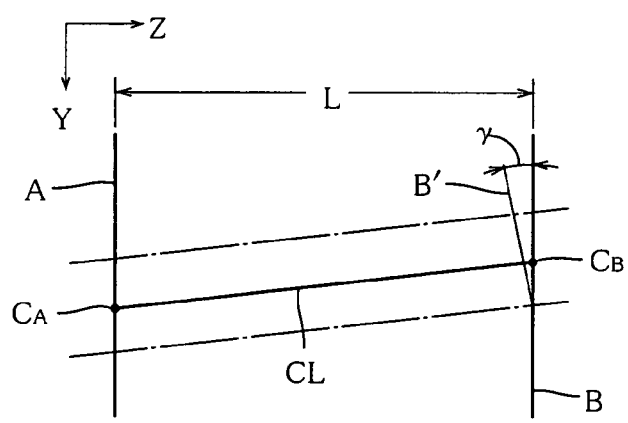
FIG. 8 is a view for explaining a cross angle, $\gamma$, at which the orthogonal section B' orthogonal to the center axis CL obtained by the center-axis calculating means, shown in FIG. 4, and the measuring section B of the second array cross each other on a plane orthogonal to the contact surface.

A center-axis calculating means or device 54 calculates a center point, $C_A$ $(X_{OA}, Y_{OA}, Z_A)$, of the closed line K on the measuring section A, and a center point, $C_B$ $(X_{OB}, Y_{OB}, Z_B)$, of the closed line K on the measuring section B, based on the respective closed lines K on the measuring sections A, B, obtained by the measuring-section-shape calculating means 52. Moreover, the center-axis calculating means 54 iteratively determines, as a center axis CL of the brachial artery 18, a straight line passing through the thus calculated respective center points $C_A$ $(X_{OA}, Y_{OA}, Z_A)$, $C_B$ $(X_{OB}, Y_{OB}, Z_B)$ of the respective closed lines K on the two measuring sections A, B. FIG. 7 shows the center axis CL projected onto a plane (i.e., a horizontal plane) parallel to the contact surface 22; and FIG. 8 shows the center axis CL projected onto a plane (i.e., a vertical plane) perpendicular to the contact surface 22. For example, unknown quantities, $X_O$, $Y_O$, of the center point $C_A$ are calculated by least square method, according to the following expression (1), i.e., an elliptic function approximating the closed line K on the measuring section A:

$$[(X_i-X_0)\cos\theta+(Y_i-Y_0)\sin\theta]^2/a^2+[(X_i-X_0)\sin\theta+(Y_i-Y_0)\cos\theta]^2/b^2=1 \quad (1)$$

A cross-angle calculating means or device 56 determines, with respect to the plane, shown in FIG. 7, parallel to the contact surface 22, an orthogonal section A' of the brachial artery 18 that passes through the center point $C_A$ of the measuring section A and is orthogonal to the center axis CL of the brachial artery 18, calculated by the center-axis calculating means 54, or an orthogonal section B' of the brachial artery 18 that passes through the center point $C_B$ of the measuring section B and is orthogonal to the center axis CL of the brachial artery 18, and iteratively calculates a cross angle, β (degrees), at which the orthogonal section A' and the measuring section A cross each other, or the orthogonal section B' and the measuring section B cross each other. Similarly, the cross-angle calculating means 56 determines, with respect to the plane, shown in FIG. 8, perpendicular to the contact surface 22, an orthogonal section A' of the brachial artery 18 that passes through the center point $C_A$ of the measuring section A and is orthogonal to the center axis CL of the brachial artery 18, calculated by the center axis calculating means 54, or an orthogonal section B' of the brachial artery 18 that passes through the center point $C_B$ of the measuring section B and is orthogonal to the center axis CL of the brachial artery 18, and iteratively calculates a cross angle, γ (degrees), at which the orthogonal section A' and the measuring section A cross each other, or the orthogonal section B' and the measuring section B cross each other.

A correcting means or device 58 corrects, based on the cross angles β, γ calculated by the cross-angle calculating means 56, each of the two shapes calculated by the measuring-section-shape calculating means 52, into a shape on a corresponding one of the two orthogonal sections A', B'. More specifically described, the correcting means 58 iteratively corrects, according to the following, correcting expressions (2), (3), the length 2b of the major axis, and the length 2a of the minor axis, of each of the two closed lines K, calculated by the measuring-section-shape calculating means 52, into a corrected length 2b' of a major axis, and a corrected length 2a' of a minor axis, on a corresponding one of the orthogonal sections A', B' of the brachial artery 18.

$$a' = a/\cos \beta \quad (2)$$

$$b' = b/\cos \gamma \quad (3)$$

where $\cos \beta = (X_0A - X_0B)/L$ and $\cos \gamma = (X_0A - X_0B)/L$

An orthogonal-section-area calculating means or device 60 iteratively calculates, based on the length 2b' of the major axis, and the length 2a' of the minor axis, on each of the orthogonal sections A', B', calculated by the correcting means 58, a corresponding one of an area, $S_A'$, of the lumen of the brachial artery 18 on the orthogonal section A', and an area, $S_B'$, of the lumen of the brachial artery 18 on the orthogonal section B'. For example, the orthogonal-section-area calculating means 60 calculates each of the area $S_A'$ and the area $S_B'$ by integrating the following expression (4), i.e., an elliptic function defined by the corrected major-axis length 2b' and the corrected minor-axis length 2a' on a corresponding one of the orthogonal sections A', B':

$$((X_i' - X_0)/a')^2 + ((Y_i' - Y_0)/b')^2 = 1 \quad (4)$$

In the present embodiment, the measuring-section-shape calculating means 52, the center-axis calculating means 54, the cross-angle calculating means 56, the correcting means 58, and the orthogonal-section-area calculating means 60 cooperate with each other to constitute a blood-vessel-shape calculating means or device 62.

An active-element calculating means or device 64 selects, based on a position of the center axis CL of the brachial artery 18 obtained by the center-axis calculating means 54, an active element, i.e., one of the supersonic-wave elements $30_n$ of the third array 30 that is the nearest to the brachial artery 18, i.e., emits a supersonic wave along a straight line that is the nearest to the center axis CL of the brachial artery 18.

A blood-flow-velocity calculating means or device 66 calculates, according to the following expression (5) pre-stored in the memory device, a maximum instantaneous blood flow velocity, $U_{max}$, corresponding to each heart beat, based on a frequency, fd, of a Doppler reflection wave whose phase or frequency has been changed by a blood flow because of Doppler effect, from that of the supersonic wave emitted by the above-described active element.

$$fd = -(fc/c)(\cos \theta_1 \cos \theta_2 + \cos \theta_3 \cos \theta_2) \quad (5)$$

Figure 9:
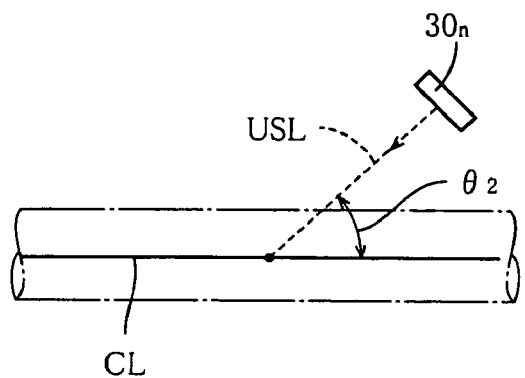
FIG. 9 is a view for explaining a relative angle, $\theta_2$, contained by the center axis CL obtained by the center-axis calculating means, shown in FIG. 4, and an emission direction, USL, in which a Doppler supersonic-wave element emits a supersonic wave, on the plane orthogonal to the contact surface.
Figure 10:
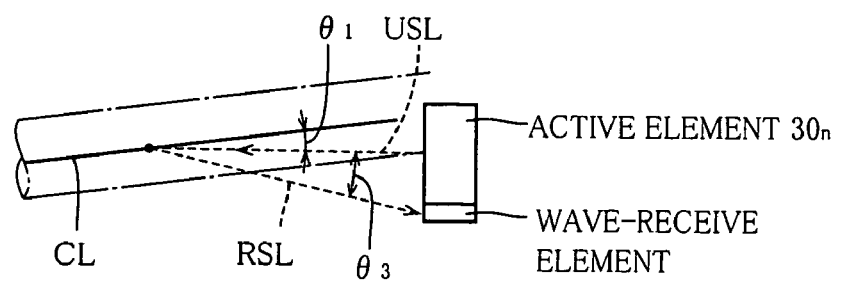
FIG. 10 is a view for explaining a relative angle, $\theta_1$, contained by the center axis CL obtained by the center-axis calculating means, shown in FIG. 4, and the emission direction USL of the Doppler supersonic-wave element, on the plane parallel to the contact surface, and a relative angle, $\theta_3$, contained by the center axis CL and a reception direction, RSL, in which the Doppler supersonic-wave element receives a wave, on the plane parallel to the contact surface.

In the expression (5), fc is a wave number of the emitted supersonic wave; and c is a velocity of a sound propagating in a body tissue. Also, in the expression (5), $\theta_2$ is an angle contained by an emission direction, USL, in which the active element emits the supersonic wave, and the center axis CL, on the plane, shown in FIG. 9, perpendicular to the contact surface 22; $\theta_1$ is an angle contained by the emission direction USL and the center axis CL, on a plane, shown in FIG. 10, parallel to the contact surface 22; and $\theta_3$ is an angle contained by a reception direction, RSL, in which a wave-receive element receives the reflection wave, and the center axis CL, on the plane, shown in FIG. 10, parallel to the contact surface 22. If the active element also functions as the wave-receive element, then the angle $\theta_3$ is equal to zero ($\theta_3 = 0$). The angles $\theta_1$, $\theta_2$, $\theta_3$ are calculated, in advance, based on a known geometrical position of the active element, and the center axis CL calculated by the center-axis calculating means 54. Thus, the expression (5) reflects corrections based on the angles $\theta_1$, $\theta_2$, $\theta_3$. That is, the blood-flow-velocity calculating means 66 calculates, according to the expression (5), a maximum instantaneous blood flow velocity $U_{max}$, while correcting errors thereof that may be caused by the relative angles $\theta_1$, $\theta_2$, $\theta_3$ between the emission direction USL and the center axis CL. Therefore, in the present embodiment, the blood-flow-velocity calculating means 66 functions as not only a relative-angle calculating means or device 68 that calculates the relative angles $\theta_1$, $\theta_2$, $\theta_3$ between the emission direction USL and the center axis CL, but also a blood-flow-velocity correcting means or device 70 that corrects the errors of maximum instantaneous blood flow velocity $U_{max}$, caused by the relative angles $\theta_1$, $\theta_2$, $\theta_3$. However, the blood-flow-velocity calculating means 66, the relative-angle calculating means 68, and the blood-flow-velocity correcting means 70 may be modified to share respective independent roles, such that the blood-flow-velocity calculating means 66 calculates a maximum instantaneous blood flow velocity $U_{max}$ without any corrections, the relative-angle calculating means 68 calculates relative angles $\theta_1$, $\theta_2$, $\theta_3$ between the emission direction USL and the center axis CL, based on a known geometrical position of the active element, and the center axis CL calculated by the center-axis calculating means 54; and the blood-flow-velocity correcting means 70 corrects errors of maximum instantaneous blood flow velocity $U_{max}$, caused by the relative angles $\theta_1$, $\theta_2$, $\theta_3$, and provides a corrected maximum instantaneous blood flow velocity $U_{max}$.

A blood-flow-amount calculating means or device 72 iteratively calculates, based on the area $S_B'$ of the brachial artery 18 on the orthogonal section B', calculated by the orthogonal-section-area calculating means 60, and the corrected maximum instantaneous blood flow velocity $U_{max}$ provided by the blood-flow-velocity calculating means 66, an amount, $Q_B$ ($=S_B' \times U_{max}/2$), of a blood flow through the orthogonal section B'. An output means or device 74 controls the display device 38 to display or print an image including numerals or graphs that represent the corrected major-axis length $2b'$ and minor-axis length $2a'$, the corrected blood flow velocity U, and the blood flow amount $Q_B$. In addition, the output means 74 stores those data in the memory device, not shown.

Figure 11:
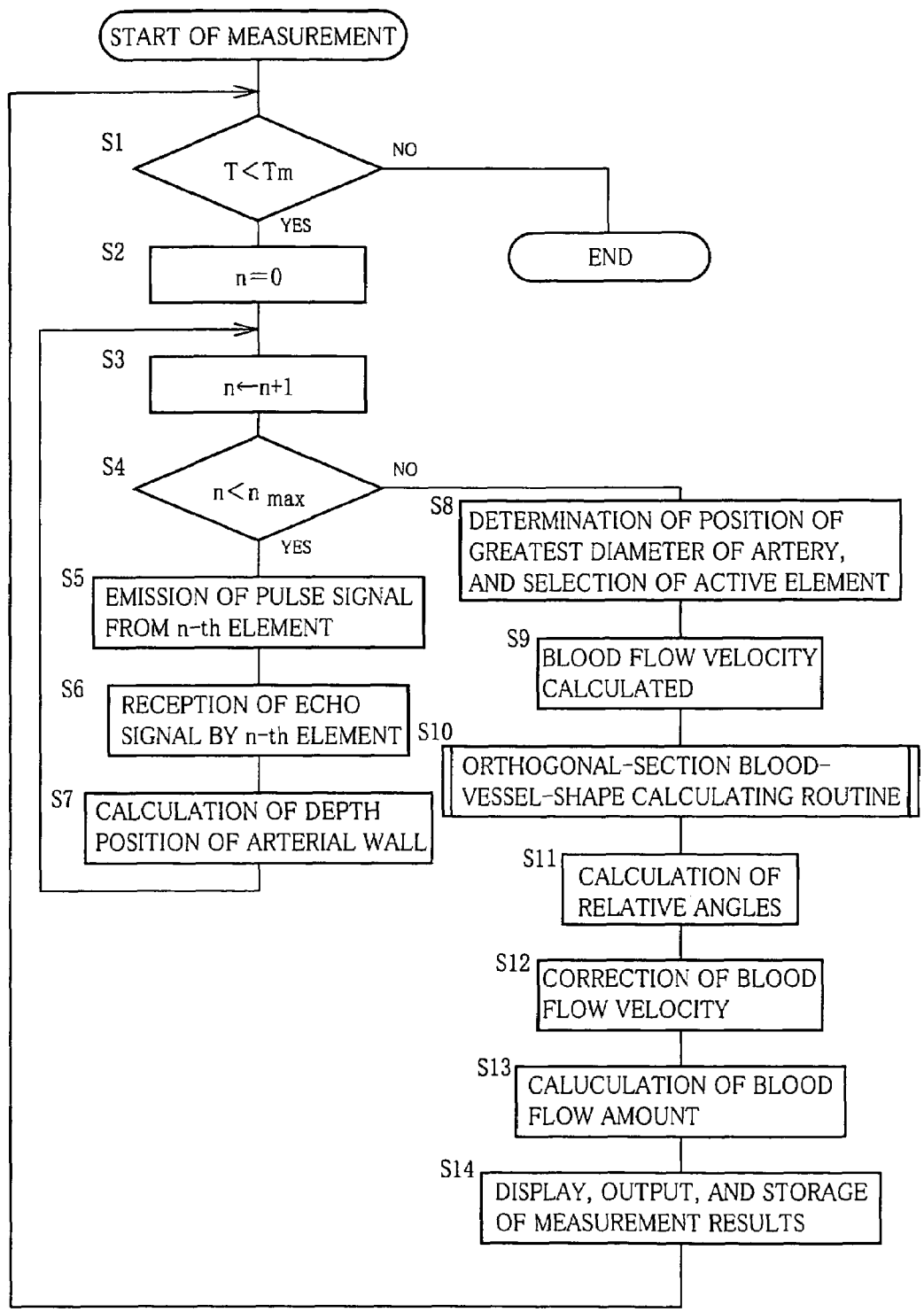
FIG. 11 is a flow chart for explaining a relevant portion of a controlling operation of the electronic control device of FIG. 3.
Figure 12:
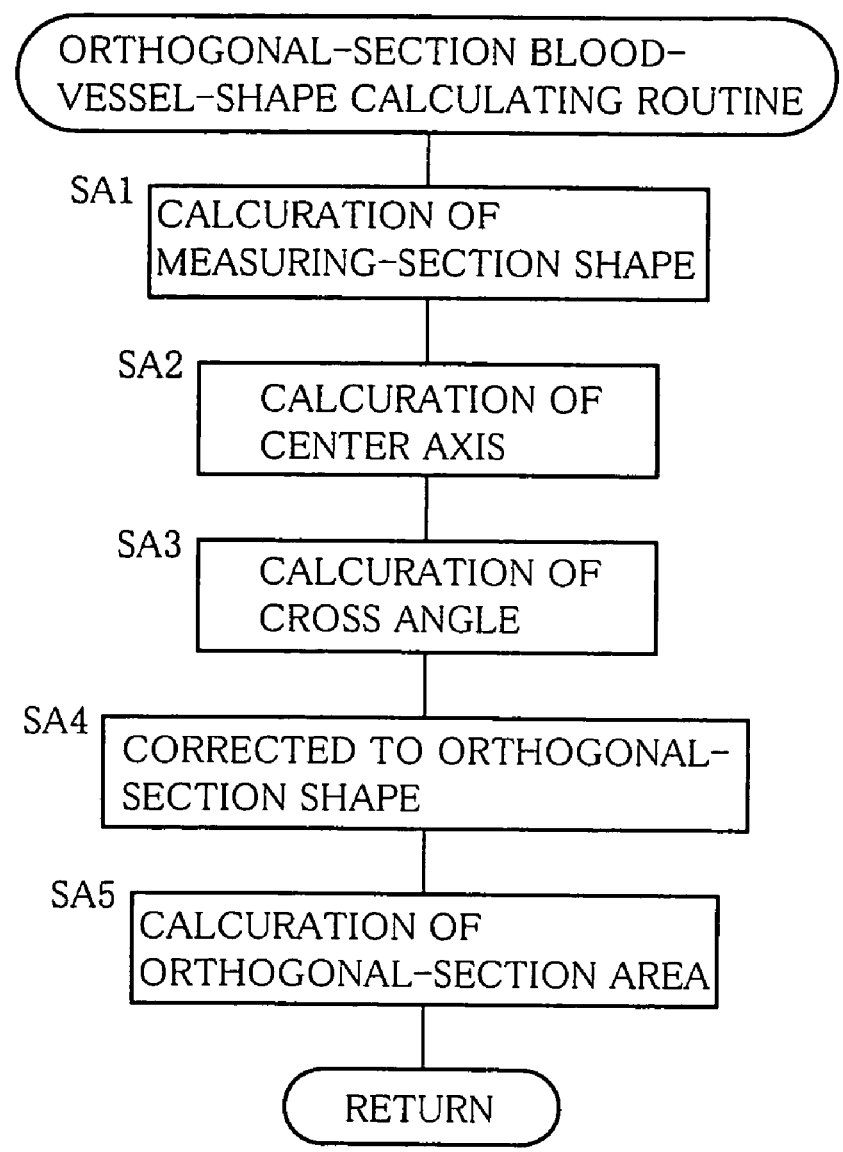
FIG. 12 is a flow chart for explaining a routine that is implemented, at Step S10 of FIG. 11, to calculate a shape of a blood vessel on an orthogonal section thereof.

FIGS. 11 and 12 show flow charts representing a relevant portion of a controlling operation of the electronic control device 36. More specifically described, FIG. 11 shows a measurement controlling routine that is implemented after a measurement starting operation is detected; and FIG. 12 shows an orthogonal-section blood-vessel-shape calculating routine as a portion of the measurement controlling routine.

In FIG. 11, when a measurement starting operation is detected, the control device 36 judges, at Step S1, whether an actual measurement time, T, is shorter than a pre-set maximum measurement time, Tm. Initially, a positive judgment is made at Step S1, and the control of the control device 36 goes to Step S2 to reset the element number, n, to zero, and then goes to Step S3 to add "1" to the element number n. Subsequently, the control goes to Step S4 to judge whether the element number n is smaller than a maximum element number, $n_{max}$, corresponding to the total number of the supersonic-wave elements $26_n$, $28_n$ of the first or second array 26, 28. Initially, a positive judgment is made at Step S4, and the control goes to Step S5 to control each of the n-th supersonic-wave element $26_n$ and the n-th supersonic-wave element $28_n$ to emit a supersonic wave, and then goes to Step S6 to control each of the n-th supersonic-wave element $26_n$ and the n-th supersonic-wave element $28_n$ to receive an echo signal. Then, the control goes to Step S7 corresponding to the first wall-position calculating means 48 and the second wall-position calculating means 50. At Step S7, the control device 36 calculates respective depth positions of respective portions of the wall of the brachial artery 18 that correspond to the n-th supersonic-wave element $26_n$ and the n-th supersonic-wave element $28_n$, respectively. Steps S3 through S7 are iteratively implemented till a negative judgment is made at Step S4.

After from the $1^{st}$ supersonic-wave elements $26_1$, $28_1$ through to the $n_{max}$-th supersonic-wave elements $26_{nmax}$, $28_{nmax}$ emit the respective supersonic waves and receive the respective echo signals, a negative judgment is made at Step S4, the control goes to Step S8 corresponding to the active-element selecting means 64. At Step S8, the control device 36 determines, based on the respective depth positions of the respective portions of the arterial wall that correspond to the supersonic-wave elements $28_n$, calculated at Step S7, a position of the greatest diameter of the brachial artery 18 on the measuring section B, or a position of the greatest depth of the arterial wall, and selects, as an active element to be used to detect a blood flow, one of the Doppler supersonic-wave elements $30_n$ of the third array 30 that is located at a position corresponding to the position of the greatest diameter of the artery 18 or the position of the greatest depth of the arterial wall. Subsequently, the control goes to Step S9 corresponding to the blood-flow-velocity calculating means 66. At Step S9, the control device 36 calculates, according to the above-described well-known expression (5), a maximum instantaneous blood flow velocity $U_{max}$, based on a frequency fd of a Doppler reflection wave whose phase or frequency has been changed by a blood flow because of Doppler effect, from that of the supersonic wave emitted by the above-described active element.

Next, at Step S10, the control device 36 implements the orthogonal-section blood-vessel-shape calculating routine shown in FIG. 12. In FIG. 12, Step SA1 corresponds to the measuring-section-shape calculating means 52. At Step SA1, the control device 36 specifies, on the X-Y coordinate plane, points representing respective depth positions of respective portions of the arterial wall that correspond to the supersonic-wave elements $26_n$, $28_n$ on each of the measuring section A and the measuring section B, as shown in FIG. 6. In addition, the control device 36 interpolates, with curved lines, the thus specified points so as to determine a closed curved line K connecting those points to each other, and determines the thus obtained closed line K as a shape of a lumen (i.e., inner hole) of the brachial artery 18. Moreover, the control device 36 calculates a major-axis length $2b$ and a minor-axis length $2a$ of the closed line K obtained on each of the measuring sections A, B. Next, the control goes to Step SA2 corresponding to the center-axis calculating means 54. At Step SA2, the control device 36 calculates, from the respective closed lines K on the two measuring sections A, B, obtained at Step SA1, a center point $C_A$ ($X_{OA}$, $Y_{OA}$, $Z_A$) of the closed line K on the measuring section A and a center point $C_B$ ($X_{OB}$, $Y_{OB}$, $Z_B$) of the closed line K on the measuring section B, and determines, as a center axis CL of the brachial artery 18, a straight line connecting between the two center points $C_A$ ($X_{OA}$, $Y_{OA}$, $Z_A$), $C_B$ ($X_{OB}$, $Y_{OB}$, $Z_B$). Subsequently, the control goes to Step SA3 corresponding to the cross-angle calculating means 56. At Step SA3, the control device 36 determines, based on the center axis CL of the brachial artery 18, calculated at Step SA2, an orthogonal section B' of the brachial artery 18 that is orthogonal to the center axis CL and passes through the center point $C_B$, with respect to the measuring section B, as illustrated in FIG. 7 showing the plane parallel to the contact surface 22. In addition, the control device 36 calculates, on the plane parallel to the contact surface 22, a cross angle β (degrees) at which the orthogonal section B' and the measuring section B cross each other. Moreover, the control device 36 calculates, on the plane perpendicular to the contact surface 22, shown in FIG. 8, a cross angle γ (degrees) at which the orthogonal section B' and the measuring section B cross each other. Then, the control goes to Step SA4 corresponding to the correcting means 58. At Step SA4, the control device 36 corrects, based on the cross angels β, γ calculated at Step SA3, the shape calculated at Step SA1, into a corrected shape on the orthogonal section B'. More specifically described, the control device 36 corrects, according to the expressions (2), (3), the major-axis length $2b$ and the minor-axis length $2a$ calculated by the measuring-section-shape calculating means 52, into a corrected major-axis length $2b'$ and a corrected minor-axis length $2a'$, respectively, on the orthogonal section B' of the brachial artery 18. Then, the control goes to Step SA5 corresponding to the orthogonal-section-area calculating means 60. At Step SA5, the control device 36 calculates, based on the corrected major-axis length $2b'$ and the corrected minor-axis length $2a'$ obtained at Step SA4, a sectional area $S_B'$ of the lumen of the brachial artery 18 on the orthogonal section B'. For example, the control device 36 calculates the sectional area $S_B'$ by integrating the expression (4) representing the ellipse defined by the corrected major-axis length $2b'$ and the corrected minor-axis length $2a'$ on the orthogonal section B'. In the present embodiment, Steps SA1 through SA5 correspond to the blood-vessel-shape calculating means 62.

Back to FIG. 11, the control further goes to Step S11 corresponding to the relative-angle calculating means 68, and Step S12 corresponding to the blood-flow-velocity correcting means 70. At those steps, the control device 36 calculates, based on the known geometrical position of the active element and the center axis CL calculated by the center-axis calculating means 54, relative angles $\theta_1$, $\theta_2$, $\theta_3$ between the center axis CL and the supersonic-wave emission direction USL, shown in FIGS. 9 and 10, and corrects errors of a maximum instantaneous blood flow velocity $U_{max}$. In the present embodiment, at Step S9, the control device 36 calculates a maximum instantaneous blood flow velocity $U_{max}$, by using the expression (5) reflecting the corrections based on the relative angles $\theta_1$, $\theta_2$, $\theta_3$. Therefore, Step S9 also functions as Steps S11 and S12.

Then, the control goes to Step S13 corresponding to the blood-flow-amount calculating means 72. At Step S13, the control device 36 calculates an amount $Q_B$ ($=S_B' \times U_{max}/2$) of a blood flow through the brachial artery 18, based on the orthogonal-section area $S_B'$ of the lumen of the artery 18 on the orthogonal section B' and the corrected maximum instantaneous blood flow velocity $U_{max}$. Then, the control goes to Step S14 corresponding to the output means 74. At Step S14, the control device 36 controls the display device 38 to display or print numerals or graphs that represent the corrected major-axis length 2b' and minor-axis length 2a', the corrected maximum instantaneous blood flow velocity $U_{max}$, and the blood flow amount $Q_B$, and additionally stores those data in the memory device, not shown. Since the major-axis length 2b' and the minor-axis length 2a' of the lumen of the brachial artery 18 on each of the orthogonal sections A', B', the sectional shape of the lumen, the orthogonal-sectional area $S_B'$ on the orthogonal section B', the maximum instantaneous blood flow velocity $U_{max}$, and the blood flow amount $Q_B$ are iteratively obtained, a sheering stress applied from the blood flow to the arterial wall can be calculated, and be utilized for evaluating the condition of endothelium.

As is apparent from the foregoing description of the present embodiment, the blood-vessel-shape calculating means 62 (S10) calculates, based on the respective echo signals detected by the first and second arrays 26, 28 placed on the skin 20 of the brachial portion 14 as the portion of the living being such that each of the first and second arrays 26, 28 is across the brachial artery 18 located under the skin 20, the respective positions of the respective portions of the arterial wall that are located right below the first and second arrays 26, 28 and correspond to the first supersonic-wave elements 26$_n$ and the second supersonic-wave elements 28$_n$, and additionally calculates, based on the respective positions of the respective portions of the arterial wall that correspond to the first and second supersonic-wave elements 26$_n$, 28$_n$, the shape of the brachial artery 18 on the orthogonal section B' thereof. Thus, even if the brachial artery 18 of the living being may run, under the skin 20, in a direction that is not perpendicular to the first or second array 26, 28 or is not parallel to the skin 20, an accurate sectional shape of the brachial artery 18 can be obtained.

In addition, in the present embodiment, the first wall-position calculating means 48 (S7) calculates the respective distances to the respective portions of the arterial wall, based on the respective time differences between the respective emission signals emitted by the first supersonic-wave elements 26$_n$ and the respective echo (i.e., reflection) signals from the respective portions of the arterial wall, detected by the first supersonic-wave elements 26$_n$, and the blood-vessel-shape calculating means 62 (S10) determines, based on the thus calculated respective distances, the respective positions of the respective portions of the arterial wall on the measuring section A of the first array 26; and the second wall-position calculating means 50 (S7) calculates the respective distances to the respective portions of the arterial wall, based on the respective time differences between the respective emission signals emitted by the second supersonic-wave elements 28$_n$ and the respective echo (i.e., reflection) signals from the respective portions of the arterial wall, detected by the second supersonic-wave elements 28$_n$, and the blood-vessel-shape calculating means 62 (S11) determines, based on the thus calculated respective distances, the respective positions of the respective portions of the arterial wall on the measuring section B of the second array 28. Therefore, the respective positions of the respective portions of the arterial wall on each of the respective measuring sections A, B of the first and second arrays 26, 28 can be obtained with accuracy.

In addition, in the present embodiment, the blood-vessel-shape calculating means 62 (S10) calculates, based on the respective positions of the respective portions of the arterial wall on each of the respective measuring sections A, B of the first and second arrays 26, 28, the center point $C_A$, $C_B$, and the major-axis length 2b and the minor-axis length 2a, of each of the respective sections of the arterial wall on the respective measuring sections of the first and second arrays 26, 28, then calculates the center axis CL of the brachial artery 18, based on the respective center points $C_A$, $C_B$ of the respective sections of the arterial wall on the respective measuring sections A, B of the first and second arrays 26, 28, subsequently calculates, based on the center axis CL of the brachial artery 18, the cross angles $\beta$, $\gamma$ at which the orthogonal section B' of the blood vessel 18 and the measuring section B cross each other, and finally corrects, based on the cross angles $\beta$, $\gamma$, the major-axis length 2b and the minor-axis length 2a, into the corrected major-axis length 2b' and the corrected minor-axis length 2a' on the orthogonal section B' of the blood vessel 18. Thus, even if the brachial artery 18 of the living being may run, under the skin 20, in the direction that is not perpendicular to the first or second array 26, 28 or is not parallel to the skin 20, an accurate sectional shape of the blood vessel 18 can be obtained.

In addition, in the present embodiment, the blood-vessel-shape calculating means 62 (S10) comprises the orthogonal-section-area calculating means 60 (SA5) that calculates the sectional area $S_B'$ of the blood vessel 18 on the orthogonal section B' thereof, based on the corrected major-axis length 2b' and the corrected minor-axis length 2a' on the orthogonal section B', provided by the correcting means 58 (SA4). Thus, even if the blood vessel 18 of the living being may run, under the skin 20, in the direction that is not perpendicular to the first or second array 26, 28 or is not parallel to the skin 20, an accurate sectional area $S_B'$ of the blood vessel 18 can be obtained.

In addition, the present measuring apparatus comprises (a) the supersonic-wave probe 12 including the first array 26 including the plurality of first supersonic-wave elements 26$_n$ arranged in one direction, the second array 28 including the plurality of second supersonic-wave elements 28$_n$ arranged in the direction parallel to the one direction, and the third array 30 including the Doppler supersonic-wave element 30$_n$, the supersonic-wave probe 12 being worn such that each of the first and second arrays 26, 28 is across the brachial artery 18 located under the skin 20 of the living being and the direction USL in which the Doppler supersonic-wave element emits the supersonic wave has the acute angle with respect to the brachial artery 18; (b) the blood-flow-velocity calculating means 66 (S9) that calculates, based on the Doppler reflection wave that is obtained when the Doppler supersonic-wave element emits the supersonic wave toward the brachial artery 18 and that is changed by a Doppler effect based on a velocity U of a blood flow in the brachial artery 18, the velocity U of the blood flow; (c) the first wall-position calculating means 48

(S7) that calculates, based on the respective echo (i.e., reflection) signals detected by the first supersonic-wave elements $26_n$ of the first array 26, the respective positions of the respective portions of the wall of the brachial artery 18 that are located right below the first array 26 and correspond to the first supersonic-wave elements $26_n$; (d) the second wall-position calculating means 50 (S7) that calculates, based on the respective echo signals detected by the second supersonic-wave elements $28_n$ of the second array 28, the respective positions of the respective portions of the arterial wall that are located right below the second array 28 and correspond to the second supersonic-wave elements $28_n$; (e) the center-axis calculating means 54 (SA2) that calculates, based on the respective positions of the respective portions of the arterial wall, calculated by the first wall-position calculating means 48, and the respective positions of the respective portions of the arterial wall, calculated by the second wall-position calculating means 50, the respective center points $C_A$, $C_B$ of the respective sections of the arterial wall on the respective measuring sections A, B of the first and second arrays 26, 28, and calculates the center axis CL of the blood vessel 18 based on the respective center points $C_A$, $C_B$ of the respective sections of the arterial wall on the respective measuring sections A, B of the first and second arrays 26, 28; (f) the relative-angle calculating means 68 (S11) that calculates the actual relative angles $\theta_1$, $\theta_2$, $\theta_3$ between the center axis CL of the blood vessel 18, calculated by the center-axis calculating means 54, and the direction USL in which the Doppler supersonic-wave element $30_n$ emits the supersonic wave toward the blood vessel 18; and (g) the blood-flow-velocity correcting means 70 that corrects, based on the actual relative angles $\theta_1$, $\theta_2$, $\theta_3$ calculated by the relative-angle calculating means 68, the velocity of the blood flow, calculated by the blood-flow-velocity calculating means 66. Thus, even if the blood vessel 18 of the living being may run, under the skin 20, in the direction that is not perpendicular to the first or second array 26, 28 or is not parallel to the skin 20, an accurate maximum instantaneous blood flow velocity $U_{max}$ in the blood vessel 18 can be obtained.

In addition, the present measuring apparatus comprises (a) the above-described constitutional elements for measuring the blood flow velocity; (b) the measuring-section-shape calculating means 52 (SA1) that calculates, based on the respective positions of the respective portions of the arterial wall, calculated by the first wall-position calculating means 48, and the respective positions of the respective portions of the arterial wall, calculated by the second wall-position calculating means 50, the center point $C_A$, $C_B$, and the major-axis length $2b$ and the minor-axis length $2a$, of each of the respective sections of the arterial wall on the respective measuring sections A, B of the first and second arrays 26, 28; (c) the cross-angle calculating means 56 (SA3) that calculates, based on the center axis CL of the blood vessel 18, calculated by the center-axis calculating means 54, the cross angles $\beta$, $\gamma$ at which the orthogonal section B' of the blood vessel 18 and the measuring section B cross each other; (d) the correcting means 58 that corrects, based on the cross angles $\beta$, $\gamma$ calculated by the cross-angle calculating means 56, the major-axis length $2b$ and the minor-axis length $2a$ calculated by the measuring-section-shape calculating means 52, into the corrected major-axis length $2b'$ and the corrected minor-axis length $2a'$ on the orthogonal section B' of the blood vessel 18; (e) the orthogonal-section-area calculating means 60 (SA5) that calculates the sectional area $S_B'$ of the blood vessel 18 on the orthogonal section B' thereof, based on the corrected major-axis length $2b'$ and the corrected minor-axis length $2a'$ on the orthogonal section B', provided by the correcting means 58; and (f) the blood-flow-amount calculating means 72 (S13) that calculates the amount $Q_B$ of the blood flow through the blood vessel 18 based on the sectional area $S_B'$ of the blood vessel 18 on the orthogonal section B' thereof, calculated by the orthogonal-section-area calculating means 60, and the maximum instantaneous blood flow velocity $U_{max}$ corrected by the blood-flow-velocity correcting means 70. Thus, even if the blood vessel 18 of the living being may run, under the skin 20, in the direction that is not perpendicular to the first or second array 26, 28 or is not parallel to the skin 20, an accurate blood flow amount $Q_B$ in the blood vessel 18 can be obtained.

While the present invention has been described in detail in its preferred embodiment by reference to the drawings, it is to be understood that the present invention may be otherwise embodied.

For example, though, in the illustrated embodiment, the blood-flow-amount calculating means 72 calculates the blood flow amount $Q_B$ ($=S_B' \times U_{max}/2$) through the orthogonal section B' of the brachial artery 18, the orthogonal-section-area calculating means 60 may be modified to calculate a sectional area $S_A'$ of the brachial artery 18 on the orthogonal section A' thereof, and the blood-flow-amount calculating means 72 may be modified to calculate a blood flow amount $Q_A$ ($=S_A' \times U_{max}/2$) through the orthogonal section A of the brachial artery 18 based on the sectional area $S_A'$ of the artery 18 on the orthogonal section A', calculated by the orthogonal-section-area calculating means 60. Alternatively, the blood-flow-amount calculating means 72 may be modified to calculate, as a blood flow amount in the blood vessel 18, an average of the blood flow amount $Q_B$ and the blood flow amount $Q_A$.

The electronic control device 36 may be adapted to calculate a pulse-wave propagation velocity based on a time difference between a change of the major-axis length $2b'$ or the minor-axis length $2a'$ of the lumen of the brachial artery 18, the sectional shape of the lumen, or the orthogonal-sectional area $S_A'$ of the lumen, each on the orthogonal section A, and a corresponding change of the major-axis length $2b'$ or the minor-axis length $2a'$ of the lumen of the artery 18, the sectional shape of the lumen, or the orthogonal-sectional area $S_B'$ of the lumen, each on the orthogonal section B'.

In the illustrated embodiment, the blood-flow-amount calculating means 72 calculates the average blood flow amount $Q_B$ ($=S_B' \times U_{max}/2$) through the orthogonal section B' of the brachial artery 18. However, in the case where the blood-flow-velocity calculating means 66 is modified to calculate an average blood flow velocity U, the blood-flow-amount calculating means 72 calculates an average blood flow amount $Q_B$ according to the following expression: $Q_B = S_B' \times U$. In addition, the blood-flow-amount calculating means 72 may be modified to calculate a maximum blood flow amount $Q_{max}$ ($=S_B' \times U_{max}$).

In the illustrated embodiment, the third array 30 is constituted by the plurality of Doppler supersonic-wave elements $30_n$. However, the third array 30 may be constituted by a single Doppler supersonic-wave element.

In the illustrated embodiment, for example, the supersonic-wave elements $26_n$ of the first array 26 emit and receive the respective supersonic waves, as shown in FIG. 5. However, it is possible to employ a so-called "beam forming technique" in which drive signals having different phases are used to operate some supersonic-wave elements to emit respective supersonic waves and thereby transmit a thin supersonic-wave beam, and some supersonic-wave elements are used to receive the beam. Since this technique allows a supersonic-wave beam to be so formed as to be converged at a predetermined distance, the detection accuracy can be improved.

The present invention is by no means limited to the above-described embodiment, and may be embodied with various changes and improvements that may occur to a person skilled in the art.

The invention claimed is:

1. A blood-vessel-shape measuring apparatus, comprising:
a first array including a plurality of first supersonic-wave elements arranged in one direction;
a second array including a plurality of second supersonic-wave elements arranged in a direction parallel to said one direction, the apparatus measuring a shape of a blood vessel of a living being, based on echo signals detected by the first and second arrays that are placed on a skin of the living being such that each of the first and second arrays is across the blood vessel located under the skin;
a first wall-position calculating means for calculating, based on respective reflection signals detected by the first supersonic-wave elements of the first array, respective positions of respective portions of a wall of the blood vessel that are located right below the first array and correspond to the first supersonic-wave elements;
a second wall-position calculating means for calculating, based on respective echo signals detected by the second supersonic-wave elements of the second array, respective positions of respective portions of the wall of the blood vessel that are located right below the second array and correspond to the second supersonic-wave elements; and
a blood-vessel-shape calculating means for calculating a shape of the blood vessel on an orthogonal section thereof, based on the respective positions of the respective portions of the wall of the blood vessel that correspond to the first supersonic-wave elements and are calculated by the first wall-position calculating means, and the respective positions of the respective portions of the wall of the blood vessel that correspond to the second supersonic-wave elements and are calculated by the second wall-position calculating means.

2. The blood-vessel-shape measuring apparatus according to claim 1, wherein the first wall-position calculating means calculates respective distances to the respective portions of the wall of the blood vessel, based on respective time differences between respective emission signals emitted by the first supersonic-wave elements and the respective reflection signals from the respective portions of the wall, detected by the first supersonic-wave elements, and determines, based on the calculated respective distances, the respective positions of the respective portions of the wall on a measuring section of the first array, and wherein the second wall-position calculating means calculates respective distances to the respective portions of the wall of the blood vessel, based on respective time differences between respective emission signals emitted by the second supersonic-wave elements and respective reflection signals from the respective portions of the wall, detected by the second supersonic-wave elements, and determines, based on the calculated respective distances, the respective positions of the respective portions of the wall on a measuring section of the second array.

3. The blood-vessel-shape measuring apparatus according to claim 2, wherein the blood-vessel-shape calculating means comprises:
a measuring-section-shape calculating means for calculating, based on the respective positions of the respective portions of the wall of the blood vessel that correspond to the first supersonic-wave elements and are calculated by the first wall-position calculating means, and the respective positions of the respective portions of the wall of the blood vessel that correspond to the second supersonic-wave elements and are calculated by the second wall-position calculating means, a center point, and a major-axis length and/or a minor-axis length, of each of a section of the wall of the blood vessel on the measuring section of the first array and a section of the wall of the blood vessel on the measuring section of the second array;
a center-axis calculating means for calculating a center axis of the blood vessel, based on the respective center points of the respective sections of the wall of the blood vessel on the respective measuring sections of the first and second arrays, calculated by the measuring-section shape calculating means;
a cross-angle calculating means for calculating, based on the center axis of the blood vessel, calculated by the center-axis calculating means, a cross angle at which the orthogonal section of the blood vessel and the measuring section cross each other; and
a correcting means for correcting, based on the cross angle calculated by the cross-angle calculating means, the major-axis length and/or the minor-axis length calculated by the measuring-section-shape calculating means, into a corrected major-axis length and/or a corrected minor-axis length on the orthogonal section of the blood vessel.

4. The blood-vessel-shape measuring apparatus according to claim 3, wherein the blood-vessel-shape calculating means comprises an orthogonal-section-area calculating means for calculating an area of the section of the blood vessel on the orthogonal section thereof, based on the corrected major-axis length and the corrected minor-axis length provided by the correcting means.

5. A blood-flow-velocity measuring apparatus, comprising:
a supersonic-wave probe including a first array including a plurality of first supersonic-wave elements arranged in one direction, a second array including a plurality of second supersonic-wave elements arranged in a direction parallel to said one direction, and a Doppler supersonic-wave element, the supersonic-wave probe being worn such that each of the first and second arrays is across a blood vessel located under a skin of a living being and a direction in which the Doppler supersonic-wave element emits a supersonic wave has an acute angle with respect to the blood vessel;
a blood-flow-velocity calculating means for calculating, based on a Doppler reflection wave which is obtained when the Doppler supersonic-wave element emits the supersonic wave toward the blood vessel and which is changed by a Doppler effect based on a velocity of a blood flow in the blood vessel, the velocity of the blood flow;
a first wall-position calculating means for calculating, based on respective reflection signals detected by the first supersonic-wave elements of the first array, respective positions of respective portions of a wall of the blood vessel that are located right below the first array and correspond to the first supersonic-wave elements;
a second wall-position calculating means for calculating, based on respective echo signals detected by the second supersonic-wave elements of the second array, respective positions of respective portions of the wall of the blood vessel that are located right below the second array and correspond to the second supersonic-wave elements;

a center-axis calculating means for calculating, based on the respective positions of the respective portions of the wall of the blood vessel that correspond to the first supersonic-wave elements and are calculated by the first wall-position calculating means, and the respective positions of the respective portions of the wall of the blood vessel that correspond to the second supersonic-wave elements and are calculated by the second wall-position calculating means, respective center points of respective sections of the wall of the blood vessel on the respective measuring sections of the first and second arrays, and calculating a center axis of the blood vessel, based on the respective center points of the respective sections of the wall of the blood vessel on the respective measuring sections of the first and second arrays;

a relative-angle calculating means for calculating an actual relative angle between the center axis of the blood vessel, calculated by the center axis calculating means, and the direction in which the Doppler supersonic-wave element emits the supersonic wave toward the blood vessel; and a blood-flow-velocity correcting means for correcting, based on the actual relative angle calculated by the relative-angle calculating means, the velocity of the blood flow calculated by the blood-flow-velocity calculating means.

6. A blood-flow-amount measuring apparatus, comprising:

the blood-flow-velocity measuring apparatus according to claim 5;

a measuring-section-shape calculating means for calculating, based on the respective positions of the respective portions of the wall of the blood vessel that correspond to the first supersonic-wave elements and are calculated by the first wall-position calculating means, and the respective positions of the respective portions of the wall of the blood vessel that correspond to the second supersonic-wave elements and are calculated by the second wall-position calculating means, a center point, and a major-axis length and/or a minor-axis length, of each of a section of the wall of the blood vessel on the measuring section of the first array and a section of the wall of the blood vessel on the measuring section of the second array;

a cross-angle calculating means for calculating, based on the center axis of the blood vessel, calculated by the center-axis calculating means, a cross angle at which the orthogonal section of the blood vessel and the measuring section cross each other;

a correcting means for correcting, based on the cross angle calculated by the cross-angle calculating means, the major-axis length and/or the minor-axis length calculated by the measuring-section-shape calculating means, into a corrected major-axis length and/or a corrected minor-axis length on the orthogonal section of the blood vessel;

an orthogonal-section-area calculating means for calculating an area of the section of the blood vessel on the orthogonal section thereof, based on the corrected major-axis length and the corrected minor-axis length provided by the correcting means; and a blood-flow-amount calculating means for calculating an amount of the blood flow in the blood vessel, based on the area of the section of the blood vessel on the orthogonal section thereof calculated by the orthogonal-section-area calculating means, and the velocity of the blood flow corrected by the blood-flow-velocity correcting means.

7. A blood-vessel-shape measuring apparatus, comprising:

a first array including a plurality of first supersonic-wave elements arranged in one direction;

a second array including a plurality of second supersonic-wave elements arranged in a direction parallel to said one direction, the apparatus measuring a shape of a blood vessel of a living being, based on echo signals detected by the first and second arrays that are placed on a skin of the living being such that each of the first and second arrays is across the blood vessel located under the skin;

a first wall-position calculating device which calculates, based on respective reflection signals detected by the first supersonic-wave elements of the first array, respective positions of respective portions of a wall of the blood vessel that are located right below the first array and correspond to the first supersonic-wave elements;

a second wall-position calculating device which calculates, based on respective echo signals detected by the second supersonic-wave elements of the second array, respective positions of respective portions of the wall of the blood vessel that are located right below the second array and correspond to the second supersonic-wave elements; and a blood-vessel-shape calculating device which calculates a shape of the blood vessel on an orthogonal section thereof, based on the respective positions of the respective portions of the wall of the blood vessel that correspond to the first supersonic-wave elements and are calculated by the first wall-position calculating device, and the respective positions of the respective portions of the wall of the blood vessel that correspond to the second supersonic-wave elements and are calculated by the second wall-position calculating device.

8. The blood-vessel-shape measuring apparatus according to claim 7, wherein the first wall-position calculating device calculates respective distances to the respective portions of the wall of the blood vessel, based on respective time differences between respective emission signals emitted by the first supersonic-wave elements and the respective reflection signals from the respective portions of the wall, detected by the first supersonic-wave elements, and determines, based on the calculated respective distances, the respective positions of the respective portions of the wall on a measuring section of the first array, and wherein the second wall-position calculating device calculates respective distances to the respective portions of the wall of the blood vessel, based on respective time differences between respective emission signals emitted by the second supersonic-wave elements and respective reflection signals from the respective portions of the wall, detected by the second supersonic-wave elements, and determines, based on the calculated respective distances, the respective positions of the respective portions of the wall on a measuring section of the second array.

9. The blood-vessel-shape measuring apparatus according to claim 8, wherein the blood-vessel-shape calculating device comprises:

a measuring-section-shape calculating device which calculates, based on the respective positions of the respective portions of the wall of the blood vessel that correspond to the first supersonic-wave elements and are calculated by the first wall-position calculating device, and the respective positions of the respective portions of the wall of the blood vessel that correspond to the second supersonic-wave elements and are calculated by the second wall-position calculating device, a center point, and a major-axis length and/or a minor-axis length, of each of a section of the wall of the blood vessel on the measuring section of the first array and a section of the wall of the blood vessel on the measuring section of the second array;

a center-axis calculating device which calculates a center axis of the blood vessel, based on the respective center points of the respective sections of the wall of the blood vessel on the respective measuring sections of the first and second arrays, calculated by the measuring-section shape calculating device;

a cross-angle calculating device which calculates, based on the center axis of the blood vessel, calculated by the center-axis calculating device, a cross angle at which the orthogonal section of the blood vessel and the measuring section cross each other; and a correcting device which corrects, based on the cross angle calculated by the cross-angle calculating device, the major-axis length and/or the minor-axis length calculated by the measuring-section-shape calculating device, into a corrected major-axis length and/or a corrected minor-axis length on the orthogonal section of the blood vessel.

10. The blood-vessel-shape measuring apparatus according to claim 9, wherein the blood-vessel-shape calculating device comprises an orthogonal-section-area calculating device which calculates an area of the section of the blood vessel on the orthogonal section thereof, based on the corrected major-axis length and the corrected minor-axis length provided by the correcting device.

11. A blood-flow-velocity measuring apparatus, comprising:

a supersonic-wave probe including a first array including a plurality of first supersonic-wave elements arranged in one direction, a second array including a plurality of second supersonic-wave elements arranged in a direction parallel to said one direction, and a Doppler supersonic-wave element, the supersonic-wave probe being worn such that each of the first and second arrays is across a blood vessel located under a skin of a living being and a direction in which the Doppler supersonic-wave element emits a supersonic wave has an acute angle with respect to the blood vessel;

a blood-flow-velocity calculating device which calculates, based on a Doppler reflection wave which is obtained when the Doppler supersonic-wave element emits the supersonic wave toward the blood vessel and which is changed by a Doppler effect based on a velocity of a blood flow in the blood vessel, the velocity of the blood flow;

a first wall-position calculating device which calculates, based on respective reflection signals detected by the first supersonic-wave elements of the first array, respective positions of respective portions of a wall of the blood vessel that are located right below the first array and correspond to the first supersonic-wave elements;

a second wall-position calculating device which calculates, based on respective echo signals detected by the second supersonic-wave elements of the second array, respective positions of respective portions of the wall of the blood vessel that are located right below the second array and correspond to the second supersonic-wave elements;

a center-axis calculating device which calculates, based on the respective positions of the respective portions of the wall of the blood vessel that correspond to the first supersonic-wave elements and are calculated by the first wall-position calculating device, and the respective positions of the respective portions of the wall of the blood vessel that correspond to the second supersonic-wave elements and are calculated by the second wall-position calculating device, respective center points of respective sections of the wall of the blood vessel on the respective measuring sections of the first and second arrays, and calculating a center axis of the blood vessel, based on the respective center points of the respective sections of the wall of the blood vessel on the respective measuring sections of the first and second arrays;

a relative-angle calculating device which calculates an actual relative angle between the center axis of the blood vessel, calculated by the center-axis calculating device, and the direction in which the Doppler supersonic-wave element emits the supersonic wave toward the blood vessel; and a blood-flow-velocity correcting device which corrects, based on the actual relative angle calculated by the relative-angle calculating device, the velocity of the blood flow calculated by the blood-flow-velocity calculating device.

12. A blood-flow-amount measuring apparatus, comprising:

the blood-flow-velocity measuring apparatus according to claim 11;

a measuring-section-shape calculating device which calculates, based on the respective positions of the respective portions of the wall of the blood vessel that correspond to the first supersonic-wave elements and are calculated by the first wall-position calculating device, and the respective positions of the respective portions of the wall of the blood vessel that correspond to the second supersonic-wave elements and are calculated by the second wall-position calculating device, a center point, and a major-axis length and/or a minor-axis length, of each of a section of the wall of the blood vessel on the measuring section of the first array and a section of the wall of the blood vessel on the measuring section of the second array;

a cross-angle calculating device which calculates, based on the center axis of the blood vessel, calculated by the center-axis calculating device, a cross angle at which the orthogonal section of the blood vessel and the measuring section cross each other;

a correcting device which corrects, based on the cross angle calculated by the cross-angle calculating device, the major-axis length and/or the minor-axis length calculated by the measuring-section-shape calculating device, into a corrected major-axis length and/or a corrected minor-axis length on the orthogonal section of the blood vessel;

an orthogonal-section-area calculating device which calculates an area of the section of the blood vessel on the orthogonal section thereof, based on the corrected major-axis length and the corrected minor-axis length provided by the correcting device; and a blood-flow-amount calculating device which calculates an amount of the blood flow in the blood vessel, based on the area of the section of the blood vessel on the orthogonal section thereof calculated by the orthogonal-section-area calculating device, and the velocity of the blood flow corrected by the blood-flow-velocity correcting device.

* * * * *